United States Patent
Hamman et al.

(10) Patent No.: US 7,883,462 B2
(45) Date of Patent: Feb. 8, 2011

(54) SUTURE RETAINER ATTACHMENT FOR USE WITH A SURGICAL RETRACTOR

(75) Inventors: Baron Hamman, Dallas, TX (US); John T. M. Wright, Denver, CO (US); Hieu Cong Nguyen, Denver, CO (US)

(73) Assignee: Genesee BioMedical, Inc., Denver, CO (US)

( * ) Notice: Subject to any disclaimer, the term of this patent is extended or adjusted under 35 U.S.C. 154(b) by 1662 days.

(21) Appl. No.: 11/119,372

(22) Filed: Apr. 29, 2005

(65) Prior Publication Data

US 2005/0245967 A1   Nov. 3, 2005

Related U.S. Application Data

(60) Provisional application No. 60/567,030, filed on Apr. 29, 2004.

(51) Int. Cl.
*A61B 1/32* (2006.01)
(52) U.S. Cl. .................................................. 600/232
(58) Field of Classification Search ......... 600/201–246; 606/105, 232, 233
See application file for complete search history.

(56) References Cited

U.S. PATENT DOCUMENTS

| | | | |
|---|---|---|---|
| 784,018 A | 2/1905 | Witherbee | |
| 3,515,129 A | 6/1970 | Truhan | |
| 3,541,591 A | 11/1970 | Hoegerman | |
| 3,952,377 A * | 4/1976 | Morell | 24/136 R |
| 3,988,810 A | 11/1976 | Emery | |
| 4,185,636 A | 1/1980 | Gabbay et al. | |
| 4,379,358 A * | 4/1983 | Wibrow | 24/136 R |
| 4,545,377 A * | 10/1985 | Cerwin et al. | 606/158 |
| 4,726,356 A * | 2/1988 | Santilli et al. | 600/232 |
| 4,852,552 A * | 8/1989 | Chaux | 600/232 |
| 5,171,251 A | 12/1992 | Bregen et al. | |
| 5,282,832 A * | 2/1994 | Toso et al. | 606/232 |
| 5,306,290 A | 4/1994 | Martins et al. | |
| 5,409,499 A | 4/1995 | Yi | |
| 5,474,572 A | 12/1995 | Hayhurst | |
| 5,514,159 A * | 5/1996 | Matula et al. | 606/232 |
| 5,630,824 A * | 5/1997 | Hart | 606/139 |
| 5,681,351 A | 10/1997 | Jamiolkowski | |
| 5,741,301 A | 4/1998 | Pagedas | |
| 5,772,583 A * | 6/1998 | Wright et al. | 600/232 |
| 5,795,291 A * | 8/1998 | Koros et al. | 600/232 |
| 5,823,946 A * | 10/1998 | Chin | 600/204 |
| RE36,289 E * | 8/1999 | Le et al. | 606/232 |

(Continued)

OTHER PUBLICATIONS

Genzyme Surgical Products Corp. (1999) Elite System Product Description Brochure.

(Continued)

*Primary Examiner*—Eduardo C Robert
*Assistant Examiner*—Mary Hoffman
(74) *Attorney, Agent, or Firm*—Swanson & Bratschun, L.L.C.

(57) ABSTRACT

A suture retainer for use with a surgical instrument comprises a slot defined in the surgical instrument, the slot having a bottom and lateral slot ends. A retainer block comprises a bottom and lateral block ends. The lateral block ends and the lateral slot ends are configured to matingly engage to define a v-shaped gap adjacent a lateral slot end near a mouth of the slot.

14 Claims, 5 Drawing Sheets

U.S. PATENT DOCUMENTS

| | | | |
|---|---|---|---|
| 6,039,176 | A | 3/2000 | Wright |
| 6,066,160 | A | 5/2000 | Colvin et al. |
| 6,126,677 | A * | 10/2000 | Ganaja et al. ............... 606/232 |
| 6,319,271 | B1 * | 11/2001 | Schwartz et al. ............ 606/232 |
| 6,475,230 | B1 * | 11/2002 | Bonutti et al. .............. 606/232 |
| 6,558,399 | B1 | 5/2003 | Isbell et al. |
| 7,147,652 | B2 * | 12/2006 | Bonutti et al. .............. 606/232 |
| 2001/0002429 | A1 * | 5/2001 | Hu et al. .................... 600/210 |
| 2001/0041827 | A1 * | 11/2001 | Spence et al. ............... 600/201 |
| 2002/0077531 | A1 * | 6/2002 | Puchovsky et al. .......... 600/229 |
| 2003/0187333 | A1 * | 10/2003 | Spence et al. ............... 600/210 |
| 2004/0260344 | A1 * | 12/2004 | Lyons et al. ................ 606/232 |
| 2005/0215863 | A1 * | 9/2005 | Ravikumar et al. ......... 600/204 |
| 2006/0270909 | A1 * | 11/2006 | Davis et al. ................. 600/210 |

OTHER PUBLICATIONS

Guidant Corp. (2002) Acrobat Off-Pump System Product Description Brochure.

Medtronic, Inc. (2000) Octobase Retractor System Product Description Brochure.

* cited by examiner

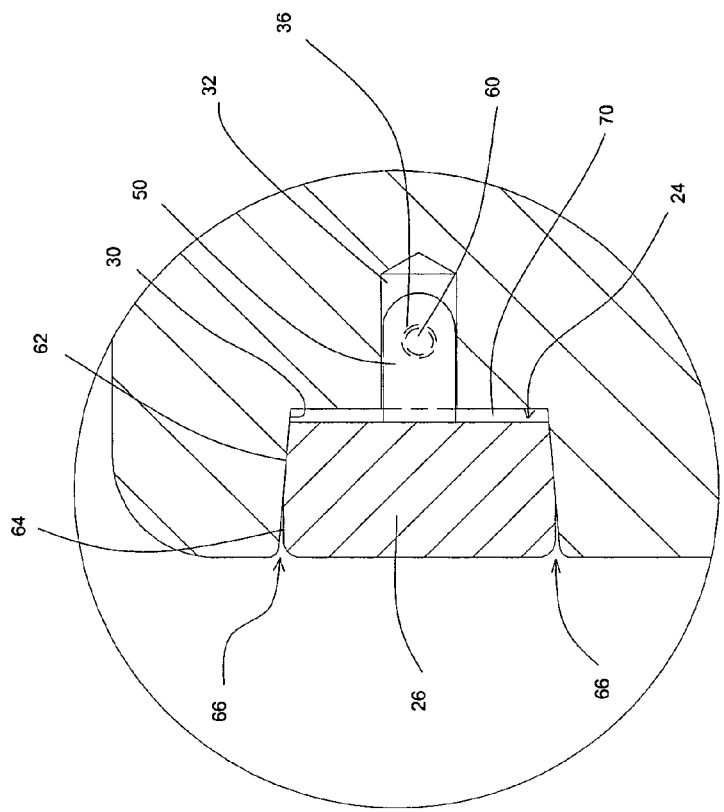
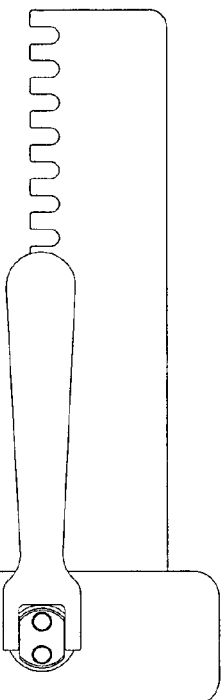
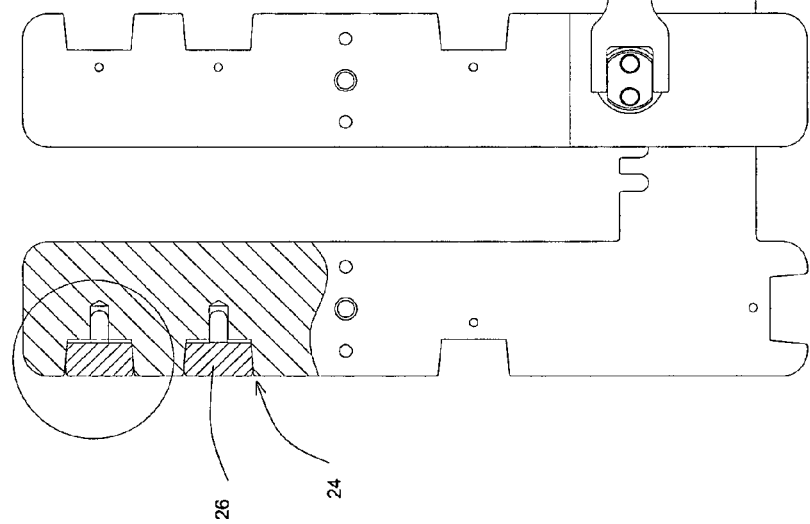
Figure 6
Figure 5

SUTURE RETAINER ATTACHMENT FOR USE WITH A SURGICAL RETRACTOR

RELATED APPLICATIONS

This application claims priority from U.S. Provisional Patent Application Ser. No. 60/567,030, filed Apr. 29, 2004, entitled "Suture Retainer Attachment for Use with a Surgical Retractor," which is hereby incorporated by reference.

TECHNICAL FIELD

The present invention is generally directed to Surgical Devices, and more particularly to a suture retainer for use with, for example, a surgical retractor.

BACKGROUND ART

Surgical retractors of various configurations are known in the art. Representative is a surgical retractor sold by Genesee Biomedical, Inc. under the trademark SRC-AR™ and which is described in Wright, U.S. Pat. No. 5,772,853, the contents of which are incorporated by reference in their entirety herein. Other examples of surgical retractors include the Genzyme-OPCAB Elite™ system sold by Genzyme Surgical Products Corporation; the Medtronic Octobase™ retractor system sold by Medtronic, Inc. and the Guidant Acrobat™ off-pump system retractor sold by Guidant Corporation.

Each of the Genzyme-OPCAB Elite™ system, the Medtronic Octobase™ retractor system and the Guidant Acrobat™ retractor system include integral suture retainers. These retractors are of particular utility in off-pump coronary artery bypass surgery. During off-pump, beating heart coronary artery, bypass surgery it is advantageous to place the patient in a steep Trendlenburg position and to elevate the apex of the left ventricle. To achieve elevation of the apex of the heart a series of surgical sutures are placed around the posterior wall of the pericardium. Typically, the sutures are made of silk or a monofilament size 2, 1 or 0. In order to maintain the apex of the heart in the desired position, the sutures must be secured to a suitable fixture such as the arms of a retractor. Thus, each of the Genzyme-OPCAB Elite™ system, the Medtronic Octobase™ retractor system and the Guidant Acrobat™ retractor system include suture retainers spaced lengthwise of the retractor arms. Ideally these suture retainers assist not only in fastening the sutures to the retractor arms to maintain the apex the heart in the desired elevated position, but also function to organize the sutures to assist in speeding the surgical procedure.

The Genzyme-OPCAB Elite™ system has channels for receiving sutures, but requires locking forceps to be used in conjunction with the channels to hold the sutures in a select position. Use of these locking forceps can complicate the surgical procedure, requires introduction of additional apparatus into an already crowded operating field and increases the time to complete a procedure by requiring manipulation of numerous locking forceps.

Both the Medtronic Octobase™ and the Guidant Acrobat™ retractors offer improvement to the Genzyme-OPCAB Elite™ system by providing self-locking suture retainers as integral elements with the surgical retractor arm for both organizing and grasping surgical sutures. In each instance the suture retainers include a cam element operatively associated with a suture channel. The cam element pivots to grasp and retain the suture within the suture channel to prevent axial withdrawal of the suture from the suture channel. While these cammed suture retainer structures offer a clear advantage over the use of locking forceps in systems like the Genzyme-OPCAB Elite™ system, use of the mechanical cam system presents some serious problems. First, these devices are disposable and relatively expensive (reusable devices would be very difficult to clean and the locking cams could be locked in a non-gripping position by dried blood or debris generated in a surgical procedure and thus rendered inoperative). In addition, the prior art locking cams have many small components that potentially might become detached and fall into the patient's chest cavity.

The present invention is directed towards overcoming one or more of the problems discussed above.

SUMMARY OF THE INVENTION

A first aspect of the present invention is a suture retainer for use with a surgical instrument. The suture retainer comprises a slot defined in the surgical instrument, the slot having a bottom and lateral slot ends. A retainer block comprises a bottom and lateral block ends. The lateral block ends and the lateral slot ends are configured to matingly engage to define a v-shaped gap adjacent a lateral slot end near a mouth of the slot. In one embodiment the slot includes lateral block ends at an obtuse angle relative to the slot bottom and the lateral block ends are at an obtuse angle relative to the block bottom substantially equal to the obtuse angle between the lateral slot ends and the slot bottom so that the retainer block fits snugly within the retainer slot. The lateral block ends further include a portion opposite the block bottom within a plane that is at an angle less than the obtuse angle relative to the block bottom to define the v-shaped gap. In another embodiment, the retainer block comprises a post extending from the block bottom and the slot in the instrument has a cavity in the bottom configured to receive the post with the lateral block ends and the lateral slot ends in abutment. This embodiment may further include the posts having first and second resilient legs biased to maintain a lengthwise gap therebetween. Each of the first and second legs has a detent extending oppositely of the detent of the other leg. The cavity in the bottom slot has opposed holes defined therein, the holes being configured to receive the post detents with the retainer block fully inserted into the retainer slot with the lateral block ends and lateral slots ends in abutment. A space may be defined between the slot bottom and the retainer block bottom with the lateral block ends and the lateral slot ends in mating abutment.

A second aspect of the invention is a suture retainer block for use with a surgical instrument, the surgical instrument defining a slot having a slot bottom between opposing lateral slot ends. The suture retainer block comprises a body having lateral block ends separated by a block bottom. The lateral block ends are configured to matingly engage with the opposing lateral slot ends near the block bottom and the slot bottom and to define a v-shaped gap adjacent the lateral slot ends near a mouth of the slot. The surgical instrument may further include a cavity defined in the slot bottom. With such an embodiment, the suture retainer block further comprises a post extending from the block bottom and configured to be received in the cavity with the lateral block ends and the lateral slot ends in abutment. The cavity in the bottom of the slot may include opposed holes defined therein. With such an embodiment the post of the suture retainer block further includes first and second resilient legs biased to maintain a lengthwise gap therebetween. Each of the first and second legs has a detent extending oppositely of the detent in the other leg. The detents are configured to be received in the holes in the cavity with the retainer block fully inserted into the retainer slot with the lateral block ends and the lateral slot ends in abutment.

The suture retainer of the present invention enables the secure attachment of sutures to a surgical instrument while enabling the suture retainer to be disassembled to permit sterilization and reuse of the surgical instrument.

BRIEF DESCRIPTION OF THE DRAWINGS

FIG. 5 is a plane view including a partial cross-section of the suture retainers of FIG. 1 in accordance with the present invention;

FIG. 6 is an enlarged cross-section view of a suture retainer of FIG. 5;

DETAILED DESCRIPTION OF THE PREFERRED EMBODIMENTS

Figure 1:
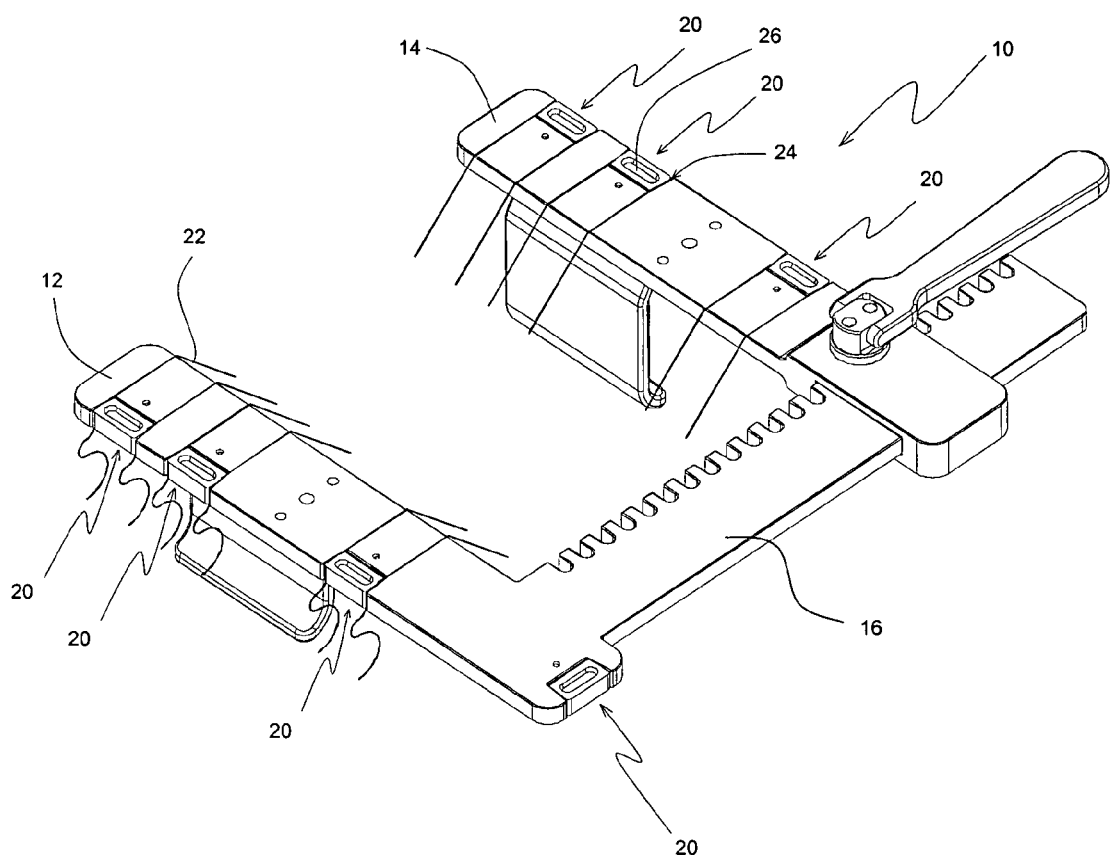
FIG. 1 is a perspective view of a surgical retractor including suture retainers in accordance with the present invention.

FIG. 1 is a perspective view of a surgical retractor including suture retainers 20 in accordance with the present invention. The surgical retractor includes a pair of opposing arms 12, 14. Similar to the retractor described in detail Wright, U.S. Pat. No. 5,772,583, the contents of which are hereby incorporated by reference herein, the arm 14 is moveable on the rack 16 relative the arm 12 to enable retraction of a sternum or thorax for gaining access for cardiovascular surgery, principally coronary artery bypass surgery carried out a beating heart. The surgical retractor is preferably made of stainless steel, but suitably rigid polymers or other metals may be used as well. Spaced lengthwise of each of the arms 12, 14 are a number of suture retainers 20. As illustrated in FIG. 1, the suture retainers 20 are retaining lengths of sutures 22, with only portions of the sutures 22 shown for the sake of clarity. Each of the suture retainers 20 consist of a retainer slot 24 (see FIG. 2) receiving a retainer block 26. The retainer slots may preferably be produced using wire electrical discharge machining for high accuracy and appropriate surface finish.

Figure 3:
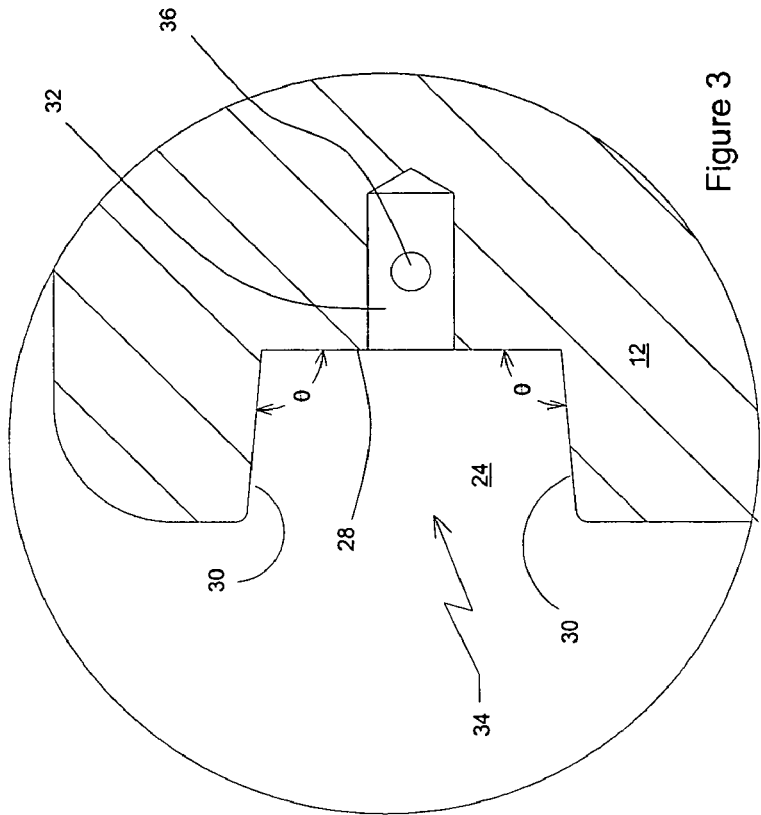
FIG. 3 is an enlarged cross-section view of a suture retainer slot of FIG. 2.
Figure 2:
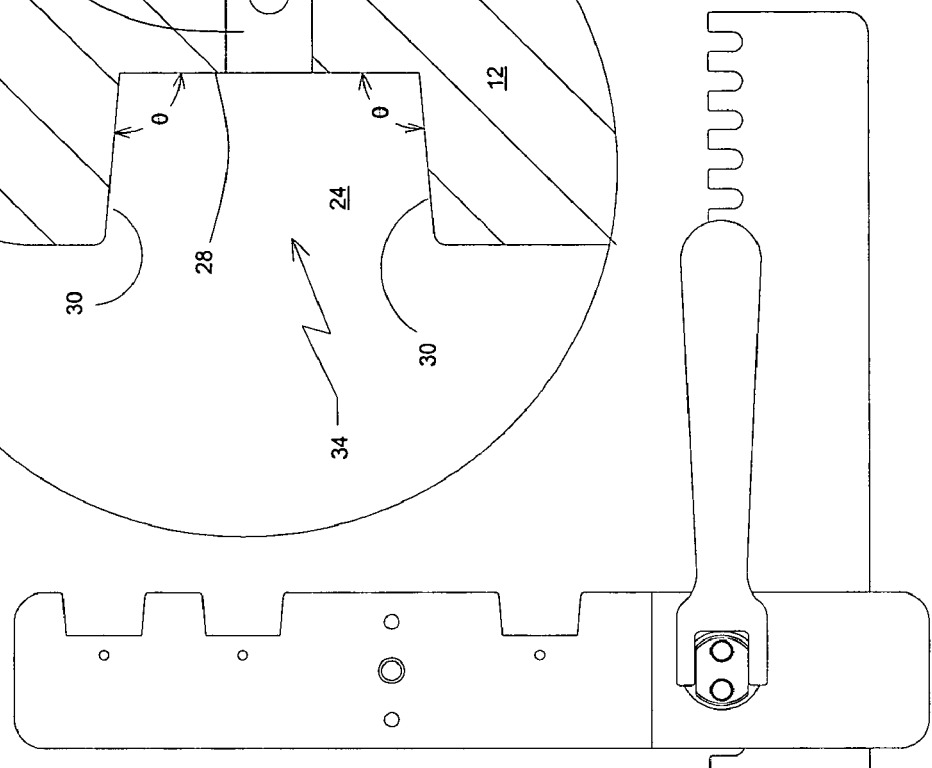
FIG. 2 is a plane view of the retractor of FIG. 1 including a partial cross-section of a suture retainer slots.

Referring to FIG. 2 and 3, the retainer slot 24 includes a slot bottom end 28 and opposing lateral slot ends 30. Referring to FIG. 3, which shows the retainer slot in a lengthwise cross-section, the retainer slot 24 further includes a cavity 32 extending into the arm 12 in a direction opposite of mouth 34 of the retainer slot 24. The cavity 32 in the slot bottom end 28 is preferable cylindrical, but can have any cross-section such as any polygon. On opposing sides of the cavity 32 are provided holes 36. In one embodiment the opposing lateral slot ends 30 are each at angle θ° that is at an obtuse angle from a plane of the retainer slot bottom end 28. An angle θ of about 95° is acceptable.

Figure 4:
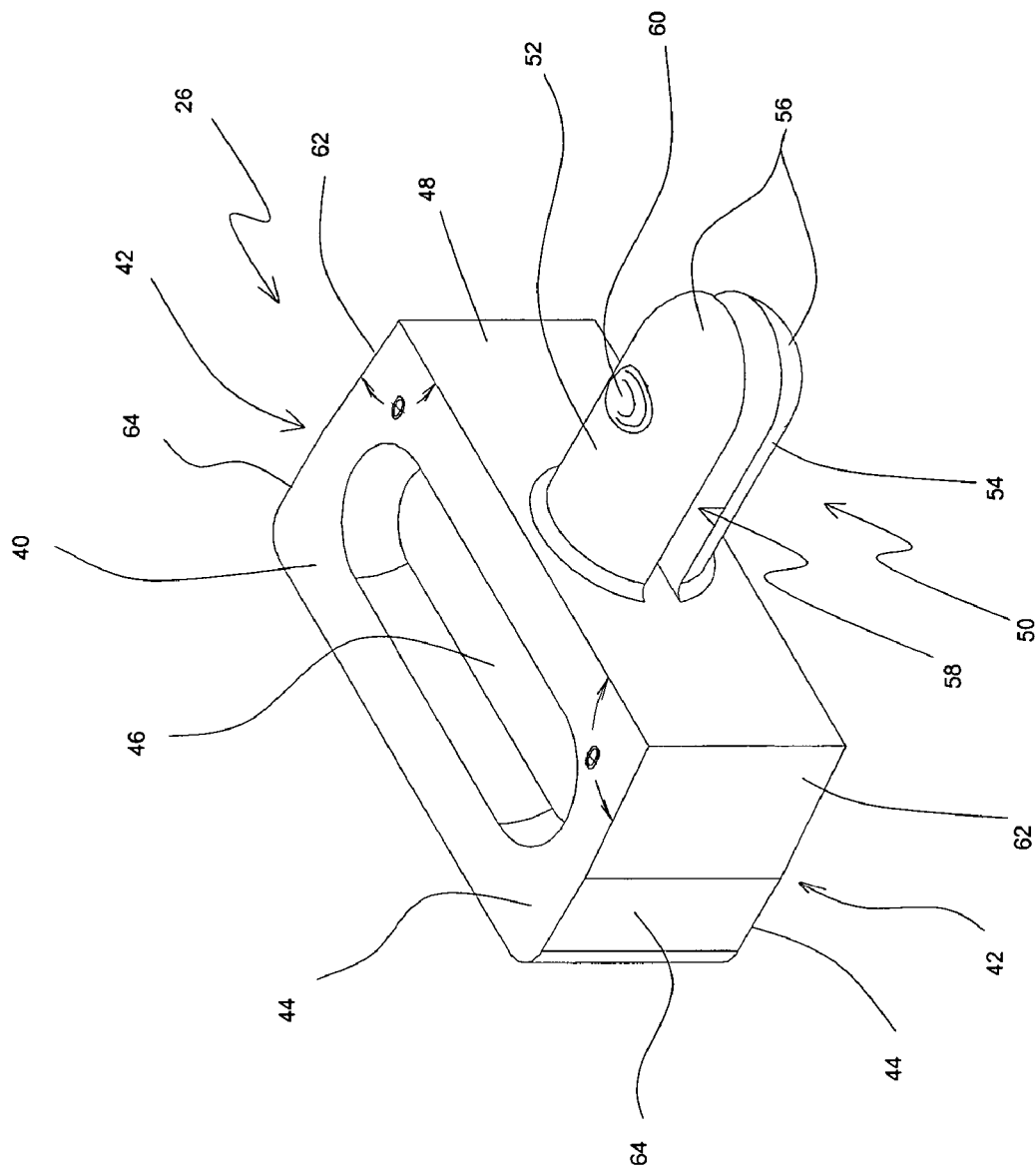
FIG. 4 is a perspective view of a suture retainer block in accordance with the present invention.

FIG. 4 is a perspective view of a retainer block 26. The retainer block 26 consists of a generally rectangular body 40 having lateral block ends 42. The retainer block 26 has a thickness that is generally equal to a thickness of the retainer arms 12, 14, as best seen in FIG. 1. The rectangular body 40 further includes sidewalls 44 having a cavity 46 configured to make it easier for user to grasp a retainer block 26 for insertion into and removal from the retainer slots 24. Extending substantially normal from a bottom wall 48 of the retainer block 26 is a post 50. In the illustrated embodiment, post 50 has a cross-section of the same shape as the cross-section of the cavity 32. In FIG. 4 the post 50 is cylindrical and has an outer diameter slightly smaller than an inner diameter of the cavity 32. The post 50 of FIG. 4 consists of semi-cylindrical first and second legs 52, 54. The distal end 56 of each of the first and second legs 52, 54 is preferably rounded. A gap 58 separates the first and second legs 52, 54. Each leg has a detent 60 that extends substantially opposite the detent of the other leg.

Each of the lateral block ends 42 has a first surface 62 and a second surface 64. Each of the first surfaces 62 are at an obtuse angle to the bottom wall 48, for example, an angle θ° substantially equal to the angle θ° (e.g., 95°) between the opposing lateral block ends 42 of the retainer slot 24 and the retainer slot bottom end 28. The second surfaces are at an angle less than θ from the plane of the bottom 48. For example, the second surfaces may be substantially parallel to each other and perpendicular to a plane of the bottom wall 48.

In one embodiment the retainer block 26 is integrally formed (i.e. injection molded) from any suitably resilient polymeric material. The polymeric material is preferably resilient enough to bias the legs 52, 54 to maintain the gap 58 between the first and second legs 52, 54. The resilient material preferably also has a coefficient of friction helping to secure a suture in the v-shaped gaps 66, yet sufficient hardness to neither wear from repeated insertion and removal of sutures nor be deformed by the sutures nor abrade the sutures. One representative material is ABS Lustron containing 20% Barium Sulfate, the latter being to render the device radiopaque.

The resilient polymer from which the retainer blocks 26 is made not only secures the pericardial sutures within the v-shaped gaps 66, it assists in securing the post legs within the receiving cavity of the retainer slot. The cavities 46 in the sidewalls of the retainer blocks 26 assist a user in griping the retainer blocks during insertion and removal of the retainer blocks from the retainer slots. Thus, a suture retainer in accordance with the present invention provides the necessary function of securing sutures while the retainer blocks are readily removable and disposable to facilitate cleaning and sterilization of the surgical retractor. If desired, ribs or other texturing can be provided in either the opposing lateral slot ends 30 or the lateral block ends 42 to enhance gripping of a suture.

FIGS. 5 and 6 illustrate retainer blocks 26 received in the retainer slots 24. Referring more particularly to FIG. 6, which shows a retainer block 26 received a retainer slot 24 in cross-section, the first surfaces 62 of the opposing lateral block ends mate with the opposing lateral slot ends 30. Clearance gap 70 ensures that precise mating between first surface 62 of the opposing lateral block ends with the opposing lateral slot ends 30, and allows for manufacturing tolerances. The post 50 is axially received in the cavity 32, and the detents 60 mate with the holes 36. The second surfaces 64 of the lateral block ends 42 along with the opposing lateral slot ends 30 define v-shaped gaps 66. In the embodiment of FIG. 6, the corresponding corners of the retainer block 26 and the retainer slot 24 are rounded to define an expanded mouth the v-shaped gaps 66. The v-shaped gaps 66 define a finely tapered receptacle for the sutures 22 which secure the sutures therein, as best seen in FIG. 1.

Figure 7:
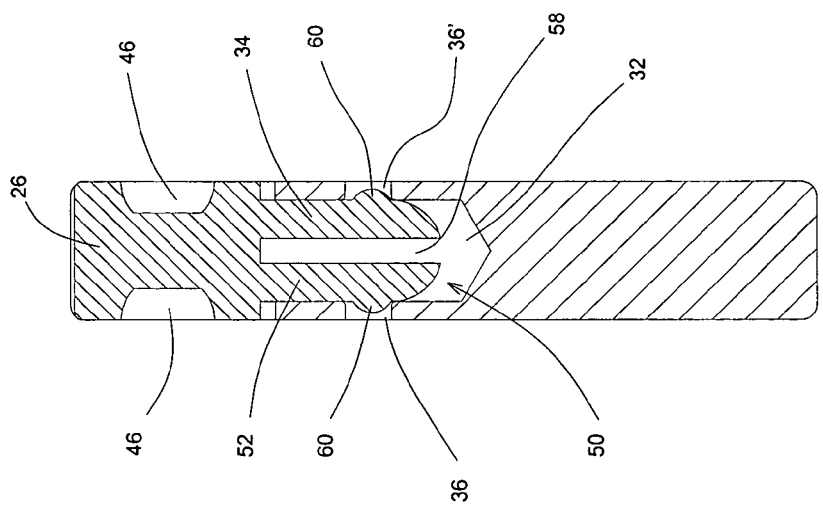
FIG. 7 is a cross-section of a suture retainer in accordance with the present invention taken at 90° from the cross-section view of FIG. 6.

FIG. 7 shows the retainer slot 24 with the retainer block 26 received therein at a cross-section rotated 90 degrees from the cross-section illustrated in FIG. 6. This cross-section illustrates the detents 60 extending into the holes 36. As described above, the retainer block 26 is preferably integrally formed of a suitable resilient polymeric material so that the first and second legs 52, 54 are biased to maintain the gap 58 there between. Thus, as the post 50 is axially inserted into the hole 32 the detents 60 cause the gap 58 to close somewhat until the detents 60 snap into the cavities 36, where upon the resiliency of the legs helps to maintain the retainer block 26 in the retainer slot 24. The cavities 46 of the retainer block 26 allow a user's finger tips to grip the retainer block 26 so as to remove it against the bias of the first and second legs 52, 54. Referring to FIG. 6, in the illustrated embodiment the tolerances between the retainer block 26 and the retainer slot 24 are such that the retainer block 26 is prevented from rotating relative to the retainer slot by engagement of the first surfaces 62 of the lateral block ends 42 with the opposing lateral slot ends 30 of the retainer slot 24. This stability helps maintain the v-shaped gap 66 to secure a suture therein and prevents rotation about the axis of the post 50.

In use, the retainer blocks 26 are axially inserted into the retainer slots as described above in advance of performing a surgical procedure. Sutures can then be attached to tissue to be elevated and secured in place by jamming the suture into the v-shaped gaps 66. To remove a suture from the v-shaped gap, a surgeon need only grab the free end of the suture and pull it out of the v-shaped gap. Following a surgical procedure, each of the retainer blocks 26 are removed and discarded. The retractor can then be relatively easily cleaned and sterilized with little concern for the suture retainers trapping blood or other disease vectors.

Figure 8:
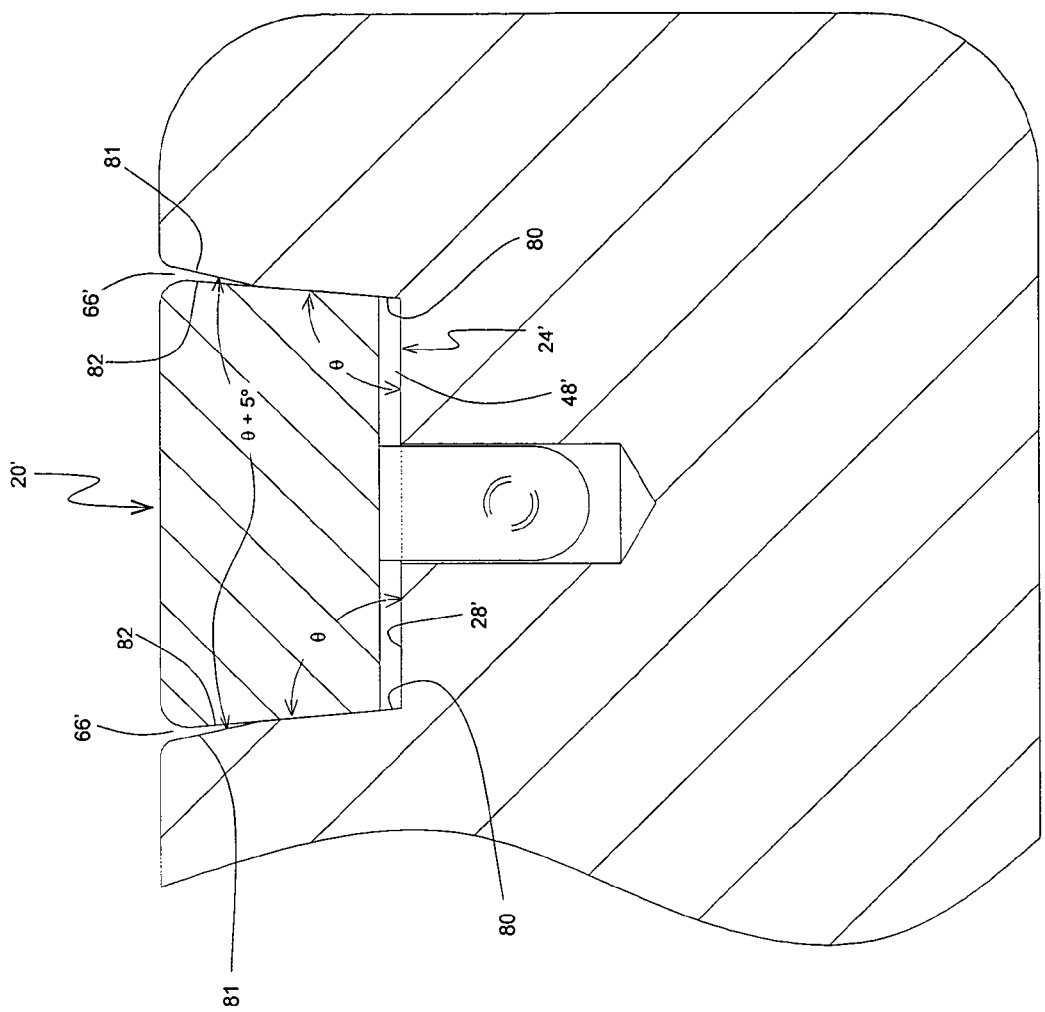
FIG. 8 is a cross-section of an alternate embodiment of a suture retainer in accordance with the present invention.

FIG. 8, illustrates a second embodiment of the suture retainer 20' in accordance with the present invention. In the embodiment shown in FIG. 8, the opposing lateral slot ends 24' are comprised of first surface 80 and second surface 81. Each of the first surfaces 80 are at an obtuse angle to the bottom wall 28', for example, an angle θ° of about 95°. Each of the second surfaces 81 are at an obtuse angle to the bottom wall 48, for example, an angle θ°+5° or about 100°.

Each of the lateral block ends 42 has a surface 82. Each of the surfaces 82 are at an obtuse angle to the bottom wall 48', preferably an angle θ° substantially equal to the angle θ° between the opposing lateral block ends 80 of the retainer slot face 80 and the retainer slot bottom end 28.

The second surfaces 81 of the lateral slot ends 24' are in a plane at an acute angle to the plane of the lateral block end wall 83, so as to define v-shaped grooves 66'.

What is claimed is:

1. A suture retainer comprising:
   a slot defined in a surgical instrument, the slot having a slot bottom, an opposing mouth and lateral slot ends; and
   a retainer block having a block bottom and lateral block ends corresponding to the slot bottom and lateral slot ends received in the slot, the lateral block ends and the lateral slot ends being configured to matingly engage to define a v-shaped gap having a linear length adjacent at least one of the lateral slot ends near the mouth of the slot, the v-shaped gap being configured to secure a linear length of a suture therein by engaging the linear length of suture inserted by lateral movement of the linear length of suture into the mouth of the V-shaped gap, wherein the lateral slot ends comprise an obtuse angle relative to the slot bottom and the lateral block ends comprise an obtuse angle relative to the block bottom substantially equal to the obtuse angle between the lateral slot ends and the slot bottom so that the retainer block fits snuggly within the slot, the lateral block ends further including a portion opposite the block bottom within a plane that is at an angle less than the obtuse angle relative to the block bottom to define the v-shaped gap.

2. The suture retainer of claim 1 wherein the obtuse angle is approximately 95°.

3. The suture retainer of claim 1 wherein the angle less than the obtuse angle is approximately 90°.

4. The suture retainer of claim 1 wherein the mating relationship between the lateral block ends and the lateral slot ends prevents rotation of the retainer block relative to the slot about an axis normal to a plane of the slot bottom.

5. The suture retainer of claim 2 wherein the v-shaped gap defines an acute angle, the acute angle being sufficiently small that the v-shaped gap can trap and retain a suture therein.

6. The suture retainer of claim 1 where in the retainer block is made of a polymetric material.

7. The suture retainer of claim 1 further comprising the retainer block having a length lengthwise of the lateral block ends, the length being less than a distance between the slot bottom and the mouth of the slot.

8. The suture retainer of claim 7 further comprising a gap between the slot bottom and the block bottom end with the lateral block ends and the lateral slot ends in mating engagement.

9. A suture retainer comprising:
   a slot defined in a surgical instrument, the slot having a slot bottom, an opposing mouth and lateral slot ends; and
   a retainer block having a block bottom and lateral block ends corresponding to the slot bottom and lateral slot ends received in the slot, the lateral block ends and the lateral slot ends being configured to matingly engage to define a v-shaped gap having a linear length adjacent at least one of the lateral slot ends near the mouth of the slot, the v-shaped gap being configured to secure a linear length of a suture therein by engaging the linear length of suture inserted by lateral movement of the linear length of suture into the mouth of the V-shaped gap, wherein the retainer block comprises a post extending from the block bottom and the slot bottom has a cavity configured to receive the post with the lateral block ends and lateral slot ends in engagement.

10. The suture retainer of claim 9 wherein the post comprises first and second resilient legs biased to maintain a lengthwise gap therebetween, each of the first and second legs having a detent extending oppositely the detent of the other leg; and
   the cavity in the slot bottom has opposed holes defined therein, the holes being configured to receive the post detents with the retainer block fully inserted into the retainer slot with lateral block ends and the lateral slot ends in engagement.

11. The suture retainer of claim 10 further comprising a gap between the slot bottom and the block bottom end with the lateral block ends and the lateral slot ends in mating engagement.

12. A suture retainer comprising:
   a slot defined in a surgical instrument, the slot having a slot bottom, an opposing mouth and lateral slot ends; and
   a retainer block having a block bottom and lateral block ends corresponding to the slot bottom and lateral slot ends received in the slot, the lateral block ends and the lateral slot ends being configured to matingly engage to define a v-shaped gap having a linear length adjacent at least one of the lateral slot ends near the mouth of the slot, the v-shaped gap being configured to secure a linear length of a suture therein by engaging the linear length of suture inserted by lateral movement of the linear length of suture into the mouth of the V-shaped gap, wherein the lateral block ends each are at a first obtuse angle relative to the block bottom and the retainer slot comprises the lateral slot ends having a first portion proximate the slot bottom at an obtuse angle relative to the slot bottom substantially equal to the first obtuse angle and a second portion at a second obtuse angle relative to the slot bottom, the second obtuse angle being greater than the first obtuse angle, whereby the retainer block fits snugly within the retainer slot with the first portion of the lateral slot ends engaging the lateral block ends and with the second portion of the lateral slot ends and the lateral block ends each defining a v-shaped gap therebetween.

13. The suture retainer of claim 12 wherein the first obtuse angle is about 95° and the second obtuse angle is about 100°.

14. The suture retainer of claim 12 wherein the v-shaped gap defines an acute angle, the acute angle being sufficiently small that the v-shaped gap can trap and retain a suture therein.

* * * * *